United States Patent [19]

Wright, Jr. et al.

[11] Patent Number: 4,710,502

[45] Date of Patent: Dec. 1, 1987

[54] 3-HETEROARYLALKYL-4-QUINAZOLI-NONES

[75] Inventors: William B. Wright, Jr.; Andrew S. Tomcufcik, both of Bergen, N.J.

[73] Assignee: American Cyanamid Company, Stamford, Conn.

[21] Appl. No.: 795,022

[22] Filed: Nov. 4, 1985

[51] Int. Cl.$^4$ .................. A61K 31/505; C07D 403/06
[52] U.S. Cl. ..................................... 514/259; 544/284
[58] Field of Search ........................ 544/284; 514/259

[56] References Cited

U.S. PATENT DOCUMENTS

| | | | |
|---|---|---|---|
| 3,274,194 | 9/1966 | Hayao | 544/284 |
| 3,322,766 | 5/1967 | Schipper | 544/284 |
| 3,382,246 | 5/1968 | Suter et al. | 544/284 |
| 3,454,574 | 7/1969 | Keck et al. | 544/284 |
| 3,557,117 | 1/1971 | Shetty | 544/284 |
| 3,558,610 | 1/1971 | Breuer et al. | 544/284 |
| 4,335,127 | 6/1982 | Vandenberk et al. | 544/284 |

FOREIGN PATENT DOCUMENTS 157891 11/1968 Hungary.

OTHER PUBLICATIONS

Kishor, et al., "Chemical Abstracts", vol. 62, 1965, col. 4471c.
Hideg et al., "Chemical Abstracts", vol. 74, 1971, col. 88041a.
Vorga, et al., "Chemical Abstracts", vol. 84, 1976, col. 84:123b.
Hideg, K., et al., "Hung. Teljes 229, 2,3-Disubstituted-Quinazolines" in Chem. Abstracts, 74(17), p. 445, 88041a (1971).

Primary Examiner—Glennon H. Hollrah
Assistant Examiner—James H. Turnipseed
Attorney, Agent, or Firm—H. G. Jackson

[57] ABSTRACT

Novel 3-heteroarylalkyl-4-quinazolinones which are useful as inhibitors of thromboxane synthetase and/or as antihypertensive agents in the treatment of hypertension and myocardial ischemia.

7 Claims, No Drawings

3-HETEROARYLALKYL-4-QUINAZOLINONES

BRIEF SUMMARY OF THE INVENTION

This invention relates to new organic compounds and, more particularly, is concerned with novel 3-(ω-heteroarylalkyl)-4(3H)-quinazolinones which may be represented by the following structural formula:

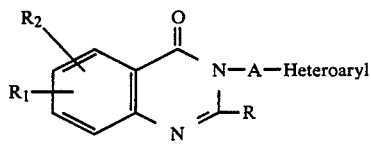

wherein A is a divalent moiety of the formula:

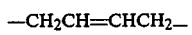

or

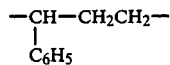

wherein n is an integer from 3 to 10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

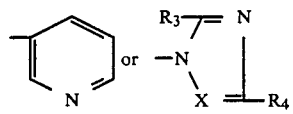

wherein $R_3$ and $R_4$ may be hydrogen, alkyl having from one to four carbon atoms or phenyl; and X is CH or N.

A preferred embodiment of the present invention may be represented by the following structural formula:

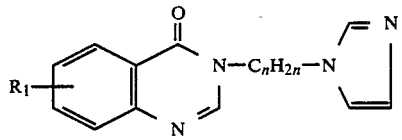

wherein $R_1$ and n are as hereinbefore defined. Most preferably, $R_1$ is chlorine and n is 4.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the like.

For purposes of this invention the free bases are equivalent to their non-toxic acid-addition salts. The acid-addition salts of the organic bases of the present invention are, in general, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction scheme wherein R, $R_1$, $R_2$, n, A and Heteroaryl are as hereinabove defined.

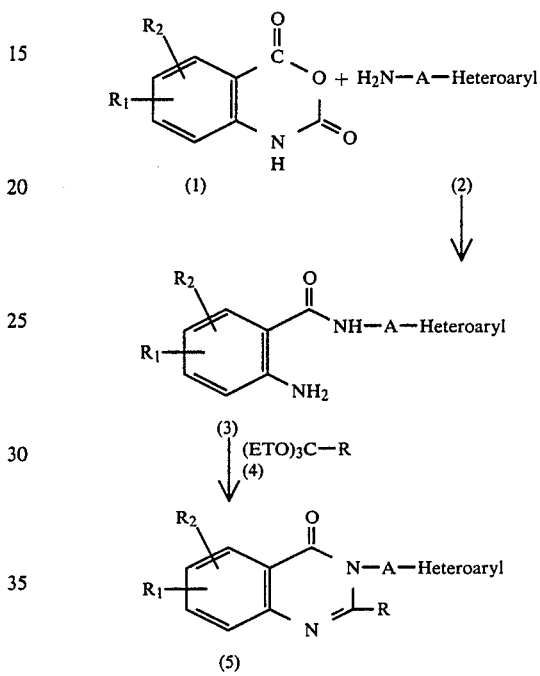

In accordance with this method, an appropriately substituted isatoic anhydride (1) is reacted with a heterocyclic alkanamine (2) in an inert solvent such as toluene, ethanol or dimethyl sulfoxide at ambient or reflux temperature to form the intermediate amide (3). Heating of (3) with an ortho ester (4) for 1-3 hours at a preferred temperature of 90°-130° C. results in the desired compounds (5).

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin, such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elsevier/North-Holland Biomedical Press, pp 137-150 (1981)]. Prostacyclin ($PGI_2$) is a potent vasodilator and platelet aggregation inhibitor, whereas thromboxane ($TXA_2$) is a powerful vasoconstrictor and inducer of platelet aggregation. $TXA_2$ synthesis is catalyzed by thromboxane synthetase enzyme located in, for example, blood platelets. When $TXA_2$ production is increased relative to $PGI_2$, platelet aggregation, thrombosis and vasopasm may occur [*Lancet* (i), 1216 (1977);

Lancet, 479 (1977); Science, 1135 (1976); Amer. J. Cardiology, 41, 787 (1978)]. TXA$_2$ synthetase inhibitors have been shown to have anti-thrombotic action superior to that of aspirin [J. Clin. Invest., 65, 400 (1980); Br. J. Pharmac., 76, 3 (1982)].

The role of prostaglandins, including TXA$_2$ and PGI$_2$, in ischemic heart patients has been reviewed [Cardiovascular Pharmacology of the Prostaglandins, A. G. Herman, P. M. Vanhoute, H. Denolin and A. Goosens, eds., Raven Press, New York, pp 361–374 (1982)]. Injection of TXA$_2$ into coronary arteries of guinea pigs and rabbits causes myocardial ischemia and subendocardial necrosis [Drugs of the Future, 7, 331 (1982); Proc. Jap. Acad., 53(B), 38 (1977); Eur. J. Pharmacol., 53 49 (1978)]. Recent research has demonstrated the beneficial effects of PGI$_2$ and selective inhibition of thromboxane synthetase on ischemic myocardium in canines [J. Cardiovascular Pharmacology, 4, 129 (1982)]. Thus compounds which selectively inhibit thromboxane synthetase (and hence TXA$_2$) without adversely affecting PGI$_2$ are useful in the treatment of vascular diseases such as ischemia and migraine. In addition, inhibition of TXA$_2$ formation may effectively treat platelet aggregation and prevent thrombosis.

From Okamoto-Aoki spontaneously hypertensive rats (SHR) (Taconic Farms, Germantown, NY) between 19 and 24 weeks in age, under urethan anesthesia, 10 μl of arterial blood was collected in one ml of 3.2% sodium citrate in a polystyrene tube. The blood was diluted with 3 ml cold saline and centrifuged at room temperature for 15 minutes at 460×g. The platelet rich plasma (PRP) was separated. The platelets were isolated by centrifuging the PRP for 10 minutes at 1060×g and were washed in 4 ml cold oxygenated Krebs phosphate buffer, pH 7.4. The chilled platelets recovered from centrifuging at 800×g for 10 minutes were resuspended in oxygenated Krebs phosphate buffer and diluted to contain 4.5–6.0×10$^4$ platelets/μl.

The inhibition of thromboxane (TX) formation was studied by determining the concentration of thromboxane B$_2$ (TXB$_2$), the stable hydrolysis product of TXA$_2$. Assay samples, prepared on ice, contained 200 μl platelet suspension, 50 μl saline, and 50 μl vehicle or drug under study at a concentration of 10$^{-4}$M (with OKY-1581, UK-3724801, 1-benzylimidazole, and/or indomethacin used as standards). The samples were incubated for 10 minutes at 37° C. in a metabolic shaker. The reaction was terminated by immersing the tubes in an ice bath and adding 50μ of 0.5M citric acid. The samples, were centrifuged for 10 minutes in a refrigerated centrifuge and the supernatants thus obtained were decanted and stored at −20° C. The TXB$_2$ content for each sample was determined by a direct radioimmunoassay (RIA) utilizing a TXB$_2$ specific RIA kit purchased from New England Nuclear, Boston, MA. and results expressed as pg TXB$_2$ formed minute$^{-1}$ sample$^{-1}$, from which the percent inhibition of TXB$_2$ formation was calculated. The results of this test on representative compounds of this invention appear in Table I below.

TABLE I

| Compound | % Inhibition |
| --- | --- |
| 3-[3-(1H—Imidazol-1-yl)propyl]-4(3H)—quinazolinone | 51 |
| 3-[4-(1H—Imidazol-1-yl)butyl]-4(3H)—quinazolinone, dihydrochloride | 83 |
| 6-Chloro-3-[4-(1H—imidazol-1-yl)butyl]-4(3H)—quinazolinone, dihydrochloride | 99 |

TABLE I-continued

| Compound | % Inhibition |
| --- | --- |
| 6-Bromo-3-[4-(1H—imidazol-1-yl)butyl]-4(3H)—quinazolinone, dihydrochloride | 99 |
| 6-Bromo-3-[3-(1H—imidazol-1-yl)propyl]-4(3H)—quinazolinone | 99 |
| 3-[3-(4-Methyl-1H—imidazol-1-yl)-propyl]-4(3H)—quinazolinone | 74 |
| 3-[3-(1H—Imidazol-1-yl)-2-methyl-propyl]-4(3H)—quinazolinone, dihydrochloride | 100 |
| 3-[4-(3-Pyridyl)butyl]-4(3H)—quinazolinone, dihydrochloride | 99 |
| 6-Chloro-3-[3-(1H—imidazol-1-yl)-propyl]-4(3H)—quinazolinone | 75 |
| 6-Chloro-3-[3-(4-methyl-1H—imidazol-1-yl)propyl]-4(3H)—quinazolinone | 89 |
| 6-Chloro-3-[3-(1H—imidazol-1-yl)butyl]-4(3H)—quinazolinone | 100 |
| 6-Chloro-3-[3-(1H—imidazol-1-yl)-2-methylpropyl]-4(3H)—quinazolinone | 94 |
| 6-Chloro-3-[4-(3-pyridyl)butyl]-4(3H)—quinazolinone | 100 |
| 3-[3-(1H—Imidazol-1-yl)butyl]-6-methyl-4(3H)—quinazolinone, dihydrochloride | 87 |
| 3-[6-(1H—Imidazol-1-yl)hexyl]-4(3H)—quinazolinone | 86 |
| 6-Chloro-3-[8-(1H—imidazol-1-yl)octyl]-4(3H)—quinazolinone | 70 |
| 6-Chloro-3-[3-(2-phenyl-1H—imidazol-1-yl)propyl]-4(3H)—quinazolinone, dihydrochloride | 96 |
| 6-Chloro-3-[3-(1H—imidazol-1-yl)-1-phenylpropyl]-4-(3H)—quinazolinone | 79 |
| 6-Bromo-3-[4-(3-pyridyl)butyl]-4(3H)—quinazolinone | 99 |

The novel compounds of the present invention are also active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y. having an average mean arterial blood pressure of 160±1.5 mm of mercury were used in the test. One to 3 rats were used per test compound. The rats were dosed by gavage with a test compound, suspended in 2% pre-boiled starch at a a concentration of 50 mg/ml, at a dose of 100 mg/kg of body weight or less, with 0.9% sodium chloride loading at a dose of 25 ml/kg of body weight. A second identical dose of the test compound, without sodium chloride loading was given 24 hours later. At 28 hours after the initial dose, the mean arterial blood pressure (MABP) was measured by the method of Chan and Poorvin vide supra. The procedure was repeated in a second and third rat when necessary as specified in the referenced method.

The results of this test on representative compounds of the present invention appear in Table II below.

TABLE II

| Product | MABP/mm Hg (no. of rats) |
| --- | --- |
| 3-[3-(1H—Imidazol-1-yl)propyl]-4(3H)—quinazolinone | 139(2) |
| 3-[4-(1H—Imidazol-1-yl)butyl]-4(3H)—quinazolinone, dihydrochloride | 117(3) |
| 6-Chloro-3-[4-(1H—imidazol-1-yl)butyl]-4(3H)—quinazolinone, dihydrochloride | 106(2) |
| 6-Bromo-3-[4-(1H—imidazol-1-yl)butyl]-4(3H)—quinazolinone, dihydrochloride | 121(2) |
| 6-Bromo-3-[3-(1H—imidazol-1-yl)propyl]-4(3H)—quinazolinone | 122(2) |

TABLE II-continued

| Product | MABP/mm Hg (no. of rats) |
|---|---|
| 3-[3-(1H—Imidazol-1-yl)butyl]-6-methyl-4(3H)—quinazolinone, dihydrochloride | 133(4) |
| 3-[3-(1H—Imidazol-1-yl)butyl]-4(3H)—quinazolinone, fumarate salt | 119(2) |
| 3-[3-(1H—Imidazol-1-yl)-2-methylpropyl]-4(3H)—quinazolinone, dihydrochloride | 121(2) |
| 6-Chloro-3-[3-(1H—imidazol-1-yl)propyl]-4(3H)—quinazolinone | 100(2) |
| 6-Chloro-3-[3-(4-methyl-1H—imidazol-1-yl)-propyl]-4(3H)—quinazolinone | 123(3) |
| 6-Chloro-3-[3-(1H—imidazol-1-yl)butyl]-4(3H)—quinazolinone | 114(2) |
| 3-[5-(1H—Imidazol-1-yl)pentyl]-4(3H)—quinazolinone | 110(2) |
| 6-Chloro-2-ethyl-3-[3-(1H—imidazol-1-yl)propyl]-4(3H)—quinazolinone | 120(4) |
| 6-Chloro-3-[8-(1H—imidazol-1-yl)octyl]-4(3H)—quinazolinone | 118(2) |
| 7-Chloro-3-[4-(1H—imidazol-1-yl)butyl]-4(3H)—quinazolinone | 126(2) |

The novel compounds of the present invention have been found to be highly useful for inhibiting thromboxane synthetase and also for lowering elevated blood pressure in mammals when administered in amounts ranging from about 0.1 mg to about 20.0 mg/kg of body weight per day. A preferred dosage regimen for optimum results would be from about 0.5 mg to about 10.0 mg/kg of body weight per day. Dosage units are employed such that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% and about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate. A sweetening agent such as sucrose, lactose or saccharin or a flavoring agent such as peppermint, oil of wintergreen or cherry flavoring may be added. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor or the equivalents thereof. Of course, any material used in preparing any dosage unit form should be pharmaceutically pure and substantially nontoxic in the amounts employed.

The following specific examples illustrate the preparation of the compounds of the present invention.

EXAMPLE 1

2-Amino-N-[4-(1H-imidazol-1-yl)butyl]benzamide

A mixture of 1.63 g of isatoic anhydride, 1.39 g of 1H-imidazole-1-butanamine and 25 ml of ethanol was stirred at room temperature for 22 hours. The reaction mixture was concentrated and the residue was dissolved in ethyl acetate and cooled. The desired product was isolated by filtration, mp 91°–93° C.

Following the procedure of this example and using the appropriate isatoic anhydride derivative, the products of Examples 2–6 were obtained as set forth in Table III

TABLE III

| Ex. | Isatoic Anhydride | Product | mp °C. |
|---|---|---|---|
| 2 | 5-Bromo | 2-Amino-5-bromo-N—[4-(1H—imidazol-1-yl)butyl]benzamide | 108–110 |
| 3 | 5-Chloro | 2-Amino-5-chloro-N—[4-(1H—imidazol-1-yl)butyl]benzamide | 91–94 |
| 4 | 5-Methyl | 2-Amino-N—[4-(1H—imidazol-1-yl)butyl]-5-methylbenzamide | 79–81 |
| 5 | 3,4-Dimethyl | 2-Amino-3,4-dimethyl-N—[4-(1H—imidazol-1-yl)butyl]benzamide | viscous oil |
| 6 | 3,5-Dichloro | 2-Amino-3,5-dichloro-N—[4-(1H—imidazol-1-yl)butyl]benzamide | viscous oil |

EXAMPLE 7

2-Amino-N-[3-(1H-imidazol-1-yl)-2-methylpropyl]-5-methylbenzamide

A mixture of 8.85 g of 5-methylisatoic anhydride, 6.7 ml of 3-(1H-imidazol-1-yl)-2-methylpropanamine and 40 ml of dimethyl sulfoxide was stirred for 20 hours at room temperature and then treated with 100 ml of water, 25 ml of 1N sodium hydroxide and 300 ml of methylene chloride. The layers were separated and the organic layer was washed with water, dried over magnesium sulfate and concentrated. The viscous residue was triturated with ether and the desired product precipitated as a hemi-hydrate, mp 120°–122° C.

Following the procedure of this example and using the appropriate isatoic anhydride, the products of Examples 8 and 9 were obtained as set forth in Table IV below.

TABLE IV

| Ex. | Isatoic Anhydride | Product | mp °C. |
|---|---|---|---|
| 8 | 5-Bromo | 2-Amino-5-bromo-N—[3-(1H—imidazol-1-yl)-2-methylpropyl]benzamide | 166–164 |
| 9 | 5-Nitro | 2-Amino-N—[3-(1H—imidazol-1-yl)-2-methylpropyl]-5-nitrobenzamide | 157–159 |

EXAMPLE 10

2-Amino-N-[3-(1H-imidazol-1-yl)propyl]benzamide

A mixture of 2.93 g of isatoic anhydride, 2.50 g of 1H-imidazol-1-propanamine and 30 ml of toluene was heated at 90° C. for 45 minutes and cooled. The toluene layer was decanted and the residue was dissolved in methylene chloride, washed with dilute sodium hydroxide solution, water and dried over magnesium sulfate. The organic layer was concentrated to obtain the desired product, mp 107°–110° C.

EXAMPLE 11

2-Amino-5-bromo-N-[3-(1H-imidazol-1-yl)propyl]benzamide

A mixture of 9.68 g of 5-bromoisatoic anhydride, 5.0 g of 1H-imidazol-1-propanamine and 75 ml of ethanol was stirred at room temperature for 20 hours and concentrated. The residue was washed onto a filter with ethanol and washed with ether for the desired product, mp 154°–156° C.

EXAMPLE 12

1-Amino-N-[3-(1H-imidazol-1-yl)butyl]-5-methylbenzamide

When 5-methylisatoic anhydride was reacted with 3-(1H-imidazol-1-yl)butanamine by the procedure of Example 11, the above compound, mp 128°–130° C., was obtained.

EXAMPLE 13

2-Amino-5-chloro-N-[3-(1H-imidazol-1-yl)propyl]benzamide

When 5-chloroisatoic anhydride was reacted with 1H-imidazole-1-propanamine by the procedure of Example 11, the above compound, mp 155°–157° C., was obtained.

EXAMPLE 14

2-Amino-5-chloro-N-[3-(1H-1,2,4-triazol-1-yl)propyl]benzamide

When 5-chloroisatoic anhydride was reacted with 3-(1H-1,2,4-triazol-1-yl)propanamine by the procedure of Example 11, this compound, mp 116°–118° C., was obtained.

EXAMPLE 15

3-[3-(1H-Imidazol-1-yl)propyl]-4(3H)-quinazolinone

A mixture of 2.44 g of 2-amino-N-[3-(1H-imidazol-1-yl)propyl]benzamide and 5 ml of triethyl orthoformate was heated in an oil bath at 100°–120° C. for 2 hours and concentrated. The residue was recrystallized from ethyl acetate and the desired base product, mp 138°–140° C. was obtained. Treatment of the base with ethanolic hydrochloric acid produced the dihydrochloride salt, mp 240°–245° C.

Following the procedure of this example and using the appropriate benzamide, the products of Examples 16–24 were obtained as set forth in Table V below.

TABLE V

| Ex. | Benzamide | Product | mp °C. |
|---|---|---|---|
| 16 | Example 1 | 3-[4-(1H—Imidazol-1-yl)butyl]-4(3H)—quinazolinone, dihydrochloride | 239–243 |
| 17 | Example 3 | 6-Chloro-3-[4-(1H—imidazol-1-yl)butyl]-4(3H)—quinazolinone, dihydrochloride | 247–250 |
| 18 | Example 2 | 6-Bromo-3-[4-(1H—imidazol-1-yl)butyl]-4(3H)—quinazolinone, dihydrochloride | 235–240 |
| 19 | Example 11 | 6-Bromo-3-[3-(1H—imidazol-1-yl)propyl]-4(3H)—quinazolinone | 186–189 |
| 20 | Example 12 | 3-[3-(1H—Imidazol-1-yl)butyl]-6-methyl-4(3H)—quinazolinone | 249–252 |
| 21 | Example 4 | 3-[4-(1H—Imidazol-1-yl)butyl]-6-methyl-4(3H)—quinazolinone | 156–161 |
| 22 | Example 5 | 3-[4-(1H—Imidazol-1-yl)butyl]-7,8-dimethyl-4(3H)—quinazolinone | viscous oil |
| 23 | Example 6 | 6,8-Dichloro-3-[4-(1H—imidazol-1-yl)butyl]-4(3H)—quinazolinone | viscous oil |
| 24 | Example 15 | 3-[3-(1H—1,2,4-Triazol-1-yl)propyl-4(3H)—quinazolinone, dihydrochloride | 195–200 |

EXAMPLE 25

3-[3-(1H-Imidazol-1-yl)butyl]-4(3H)-quinazolinone

A mixture of 3.25 g of isatoic anhydride, 2.78 g of 3-(1H-imidazol-1-yl)butanamine and 40 ml of ethanol was stirred at room temperature for 20 hours and concentrated. The residue and 10 ml of triethyl orthoformate were heated at 95°-115° C. for 3 hours and concentrated to obtain the desired product as an oil.

The oily product was treated with one molar equivalent of fumaric acid in ethanol and the crystalline fumarate salt, mp 156°-158° C., was obtained.

When the base was treated with ethanolic hydrochloric acid, the dihydrochloride salt was obtained.

Following the procedure of this example and using the appropriate diamine intermediates, the products of Examples 26-30 were obtained as set forth in Table VI below.

TABLE VI

| Ex. | Diamine Intermediate | Product | mp °C. |
|---|---|---|---|
| 26 | 4-Methyl-1H—imidazole-1-propanamine | 3-[3-(4-Methyl-1H—imidazol-1-yl)propyl]-4(3H)—quinazolinone | 134-140 |
| 27 | 3-(1H—Imidazol-1-yl)-2-methylpropanamine | 3-[3-(1H—Imidazol-1-yl)-2-methylpropyl]-4(3H)—quinazolinone, dihydrochloride | 245-248 |
| 28 | 4-(3-Pyridyl)butanamine | 3-[4-(3-Pyridyl)butyl]-4(3H)—quinazolinone, dihydrochloride | 226-230 |
| 29 | Imidazole-1-hexanamine | 3-[6-(1H—Imidazol-1-yl)hexyl]-4(3H)—quinazolinone, dihydrochloride | 142-146 |
| 30 | Imidazole-1-pentanamine | 3-[5-(1H—Imidazol-1-yl)pentyl]-4(3H)—quinazolinone, dihydrochloride | 230-233 |

EXAMPLE 31

6-Chloro-[3-(1H-imidazol-1-yl)propyl]-4(3H)-quinazolinone

A mixture of 1.98 g of 5-chloroisatoic anhydride, 1.25 g of imidazole-3-propanamine and 20 ml of ethanol was stirred at room temperature for 20 hours and concentrated. Triethyl orthoformate, 5 ml, was added and the reaction mixture was heated in an oil bath at 110°-122° C. for 3 hours. The mixture was concentrated and the residue was recrystallized from ethanol to obtain the desired product, mp 192°-194° C.

Treatment of the above product with ethanolic hydrochloric acid results in the dihydrochloride salt.

When the above procedure was followed using the appropriate diamine intermediate, the compounds of Examples 32-41 were obtained as set forth in Table VII.

EXAMPLE 42

7-Chloro-3-[4-(1H-imidazol-1-yl)butyl]-4(3H)-quinazolinone

A mixture of 1.39 g of imidazole-4-butanamine, 1.98 g of 4-chloroisatoic anhydride and 25 ml of ethanol was left at room temperature for 20 hours and concentrated. The residue and 5 ml of triethyl orthoformate were heated in an oil bath at 100°-125° C. for 3 hours and concentrated. The mixture was treated with ether to obtain the desired product, mp 123°-125° C.

When the above was treated with ethanolic hydrochloric acid, the dihydrochloride salt was obtained, mp 223°-228° C.

When the procedure of Example 42 is followed, substituting the appropriate isatoic acid derivative, the products of Examples 43-46 are obtained as set forth in Table VIII.

TABLE VIII

| Ex. | Isatoic Anhydride | Product |
|---|---|---|
| 43 | 3-Chloro | 8-Chloro-3-[4-(1H—imidazol-1-yl)butyl]-4(3H)—quinazolinone |
| 44 | 5-Fluoro | 6-Fluoro-3-[4-(1H—imidazol-1-yl)butyl]-4(3H)—quinazolinone |
| 45 | 3-Trifluoromethyl | 3-[4-(1H—Imidazol-1-yl)butyl]-8-trifluoromethyl-4(3H)—quinazolinone |
| 46 | 5-Methoxy | 3-[4-(1H—Imidazol-1-yl)butyl]-6-methoxy-4(3H)—quinazolinone |

TABLE VII

| Ex. | Diamine Intermediate | Product | mp °C. |
|---|---|---|---|
| 32 | (4-Methyl-1H—imidazole)-1-propanamine | 6-Chloro-3-[3-(4-methyl-1H—imidazol-1-yl)propyl]-4(3H)-quinazolinone | 191-195 |
| 33 | 3-(1H—Imidazol-1-yl)-butanamine | 6-Chloro-3-[3-(1H—Imidazol-1-yl)butyl]-4(3H)—quinazolinone | 133-135 |
| 34 | 3-(1H—Imidazol-1-yl)-2-methylpropamine | 6-Chloro-3-[3-(1H—imidazol-1-yl)-2-methylpropyl]-4(3H)quinazolinone | 148-150 |
| 35 | 4-(3-Pyridyl)butanamine | 6-Chloro-3-[4-(3-pyridyl)butyl]-4(3H)—quinazolinone | 129-131 |
| 36 | Imidazol-1-octanamine | 6-Chloro-3-[8-(1H—imidazol-1-yl)octyl]-4(3H)—quinazolinone | 93-96 |
| 37 | (2-Phenyl-1H—imidazole)-1-propanamine | 6-Chloro-3-[3-(2-phenyl-1H—imidazol-1-yl)propyl]-4(3H)—quinazolinone, dihydrochloride | 226-230 |
| 38 | Imidazole-1-pentanamine | 6-Chloro-3-[5-(1H—imidazol-1-yl)pentyl]-4(3H)—quinazolinone, dihydrochloride | 205-209 |
| 39 | (4-methyl-1H—imidazole)-1-butanamine | 6-Chloro-3-[4-(4-methyl-1H—imidazol-1-yl)butyl]-4(3H)—quinazolinone | 138-140 |
| 40 | (2-methyl-1H—imidazole-1-propanamine | 6-Chloro-3-[3-(2-methyl-1H—imidazol-1-yl)propyl]-4-(3H)—quinazolinone | viscous oil |
| 41 | 3-(1H—Imidazol-1-yl)-3-phenylpropanamine | 6-Chloro-3-[3-(1H—imidazol-1-yl)-3-phenylpropyl]-4-(3H)—quinazolinone | 159-161 |

EXAMPLE 47

6-Bromo-3-[3-(1H-imidazol-1-yl)-2-methylpropyl]-4(3H)-quinazolinone)

A mixture of 3.37 g of 2-amino-5-bromo-N-[3-(1H-imidazol-1-yl)-2-methylpropyl]benzamide, 5 ml of triethyl orthoformate and 10 ml of ethanol was heated at reflux temperature for 20 hours. The reaction mixture was concentrated, triturated with ether and then boiled with ethyl acetate. The insoluble product was filtered off, mp 159°–162° C.

EXAMPLE 48

3-[3-(1H-Imidazol-1-yl)-2-methylpropyl]-6-methyl-4(3H)-quinazolinone

This compound, mp 120°–122° C., was obtained when 2-amino-N-[3(1H-imidazol-1yl)-2-methylpropyl]-5-methylbenzamide was treated with triethyl orthoformate by the procedure of Example 49.

EXAMPLE 49

6-Chloro-3-[10-(1H-imidazol-1-yl)decyl]-4(3H)-quinazolinone

A mixture of 100.0 g of 1,10-dibromodecane and 50.0 g of 1H-isoindole-1,3(2H)-dione, potassium salt in 500 ml of N,N-dimethylformamide was stirred and heated on a steam bath for eight hours. The reaction mixture was clarified while hot with activated charcoal, then filtered. The material on the filter was washed with 100 ml of N,N-dimethylformamide. The filtrate and wash were combined and taken to dryness in vacuo. The residue was triturated with 100 ml of hexane. The insoluble product was collected, washed with 50 ml of hexane, then air dried and gave 81.0 g of 2-(10-bromodecyl)-1H-isoindole-1,3(2H)-dione.

A 99.0 g amount of 2-(10-bromodecyl)-1H-isoindole-1,3(2H)-dione (prepared as described above) was dissolved in 300 ml of warm N,N-dimethylformamide with stirring. This solution was added to a stirred solution of 1H-imidazole, sodium salt (prepared by stirring a mixture of 20 g of imidazole and 14.0 g 50% sodium hydride in 500 ml of N,N-dimethylformamide at room temperature for 48 hours). The resulting mixture was heated on a steam bath for 14 hours, then taken to dryness in vacuo. The residue was partitioned between 500 ml of dichloromethane and 250 ml of water. The organic layer was washed with 250 ml of water, dried over magnesium sulfate and filtered. The filtrate was evaporated in vacuo and gave 85.4 g of 2-[10-(1H-imidazol-1-yl)decyl]-1H-isoindole-1,3(2H)-dione as an oil which solidified on standing at room temperature.

The above product (85.4 g) was dissolved in one liter of hot ethanol, 17.0 ml of hydrazine hydrate was added and the mixture was heated at reflux for 25 hours. The reaction mixture was filtered hot. The precipitate collected was extracted successively with 300 ml of hot hydrochloric acid, 300 ml of hot water, then 300 ml of water. The preceding filtrate was taken to dryness in vacuo and the resulting residue was mixed with the combined acid-water extracts (900 ml) and heated to the boil. The mixture was filtered while hot and the material on the filter was washed with 300 ml of hot water. The above filtrate and water wash were combined, heated to a boil, treated with activated charcoal and filtered. The filtrate was evaporated to dryness in vacuo. The resulting waxy residue was partitioned between 300 ml of methylene chloride and 200 ml of 5N sodium hydroxide. The organic layer was dried over magnesium sulfate and filtered. The filtrate was evaporated in vacuo and gave 38.1 g of 10-(1H-imidazol-1-yl)octylamine as an oil.

A mixture of 4.47 g of the above oil, 20 ml of dimethyl sulfoxide and 3.96 g of 5-chloroisatoic anhydride was stirred for 20 hours at room temperature. The reaction mixture was treated with 40 ml of water, 10 ml of 1N sodium hydroxide and 100 ml of methylene chloride and the layers were separated. The organic layer was washed with water, dried over magnesium sulfate and concentrated.

The above crude, 20 ml of ethanol and 10 ml of triethyl orthoformate were heated at reflux temperature for 20 hours and concentrated to obtain the desired product as an oil.

EXAMPLE 50

6-Chloro-3-[3-(1H-imidazol-1-yl)-propyl]-2-methyl-4-(3H)-quinazolinone

A mixture of 2.79 g of 2-amino-5-chloro-N-[3-(1H-imidazol-1-yl)propyl]benzamide, 5 ml of trimethyl orthoacetate and 10 ml of ethyl alcohol was heated at reflux for 24 hours. The resulting solution was concentrated and the residue was triturated with ether and gave a solid. The ether was decanted and the solid was dissolved in ethyl acetate and allowed to stand. The precipitate was collected and gave 650 mg of the desired product as tan crystals, mp 190°–192° C.

EXAMPLE 51

6-Chloro-2-ethyl-3-[3-(1H-imidazol-1-yl)propyl]-4(3H)-quinazolinone

A mixture of 2.79 go of 2-amino-5-chloro-N-[3-(1H-imidazol-1-yl)propyl]benzamide, 6 ml of triethyl orthoacetate and 10 ml of ethyl alcohol was heated at reflux for 24 hours. The resulting solution was concentrated and the residue was triturated with ether and gave a gummy white solid. The solid was recrystallized from ethyl acetate and gave 780 mg of the product of the example as tan crystals, mp 147°–149° C.

EXAMPLE 52

3-[3-(1H-Imidazol-1-yl)-2-methylpropyl]-6-nitro 4(3H)-quinazolinone

A mixture of 3.03 g of 2-amino-N-[3-(1H-imidazol-1-yl)-2-methylpropyl]-5-nitrobenzamide and 10 ml of triethyl orthoformate is heated at reflux temperature for 20 hours and concentrated to obtain the above compound.

EXAMPLE 53

6-Amino-3-[3-(1H-imidazol-1-yl)-2-methylpropyl]-4(3H)-quinazolinone

A mixture of 1.7 g of 3-[3-(1H-imidazol-1-yl)-2-methylpropyl]-6-nitro-4(3H)-quinazolinone, 2.0 g of 10% palladium-on-carbon catalyst and 200 ml of ethanol is shaken in a Parr hydrogenator under 45 pounds of hydrogen pressure until the hydrogen uptake is complete. The reaction mixture is heated to the boil and the catalyst is filtered off. The ethanolic solution is concentrated to a low volume and the desired product is removed by filtration.

What is claimed is:

1. A compound selected from the group consisting of those of the formula:

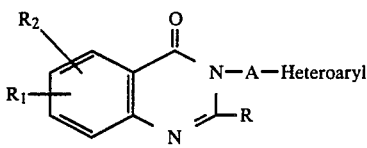

wherein A is a divalent moiety of the formula:

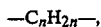

wherein n is an integer from 3 to 10, inclusive; R is hydrogen or alkyl having from one to four carbon atoms; $R_1$ and $R_2$ may be the same or different and may be selected from the group consisting of hydrogen, halogen, or trifluoromethyl provided that at least one $R_1$ or $R_2$ is halogen or trifluoromethyl; wherein Heteroaryl is

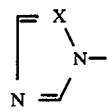

wherein X is CH or N, together with the pharmaceutically acceptable salts thereof.

2. A compound according to claim 1, wherein n is 3 or 4, and one of $R_1$ and $R_2$ is hydrogen and the other is chlorine.

3. A compound according to claim 2 which is selected from the group consisting of:
6-chloro-3-[4-(1H-imidazol-1-yl)butyl]-4(3H)-quinazolinone;
6-chloro-3-[3 -(1H-imidazol-1-yl)propyl]-4(3H)-quinazolinone;
6chloro-3-[3-(1H-imidazol-1-yl)butyl]-4(3H)quinazolinone; and
6-chloro-3-[3-1H-imidazol-1-yl)-2-methylpropyl]-4(3H)-quinazolinone.

4. The compound according to claim 1 which is 6-bromo-3-[4-(1H-imidazol-1-yl)butyl]-4(3H)-quinazolinone.

5. The compound according to claim 1 which is 6-bromo-3-[3-(1H-imidazol-1-yl)propyl]-4(3H)-quinazolinone.

6. The compound according to claim 1 which is 6-chloro-3-[8-(1H-imidazol-1-yl)octyl]-4(3H)-quinazolinone.

7. A composition of matter in dosage unit form, said composition comprising from about 10 mg to about 700 mg of a compound selected from those of the formula:

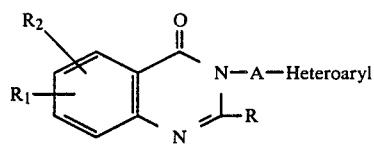

wherein A is a divalent moiety of the formula:

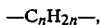

wherein n is an integer from 3 to 10, inclusive; R is hydrogen or alkyl having from one to four carbon atoms; $R_1$ and $R_2$ may be the same or different and may be selected from the group consisting of hydrogen, halogen, or trifluoromethyl provided that at least one $R_1$ or $R_2$ is halogen or trifluoromethyl; wherein Heteroaryl is

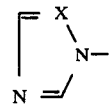

wherein X is CH or N, together with the pharmaceutically acceptable salts thereof in association with a pharmaceutically acceptable carrier.

* * * * *